(12) United States Patent
Kirking et al.

(10) Patent No.: US 6,821,299 B2
(45) Date of Patent: Nov. 23, 2004

(54) IMPLANTABLE PROSTHESIS FOR MEASURING SIX FORCE COMPONENTS

(75) Inventors: Bryan Kirking, Austin, TX (US);
Aaron Bailey, Austin, TX (US);
Robert Radefeld, Austin, TX (US);
John Green, Lincoln Park, NJ (US)

(73) Assignee: Zimmer Technology, Inc., Chicago, IL (US)

( * ) Notice: Subject to any disclaimer, the term of this patent is extended or adjusted under 35 U.S.C. 154(b) by 89 days.

(21) Appl. No.: 10/393,556

(22) Filed: Mar. 21, 2003

(65) Prior Publication Data

US 2004/0019384 A1 Jan. 29, 2004

Related U.S. Application Data

(60) Provisional application No. 60/398,335, filed on Jul. 24, 2002.

(51) Int. Cl.[7] .............................. A61F 2/38; A61B 5/103
(52) U.S. Cl. ..................................... 623/20.14; 600/587
(58) Field of Search ................ 623/20.14, 20.15–20.36; 600/587

(56) References Cited

U.S. PATENT DOCUMENTS

| | | | | | |
|---|---|---|---|---|---|
| 3,696,317 | A | * | 10/1972 | Farr | 338/5 |
| 3,915,015 | A | * | 10/1975 | Crane et al. | 73/865.4 |
| 5,125,408 | A | * | 6/1992 | Basser | 600/410 |
| 5,360,016 | A | * | 11/1994 | Kovacevic | 600/595 |
| 5,425,775 | A | * | 6/1995 | Kovacevic et al. | 128/898 |
| 5,456,724 | A | * | 10/1995 | Yen et al. | 623/23.49 |
| 5,470,354 | A | * | 11/1995 | Hershberger et al. | 128/898 |
| 5,733,292 | A | * | 3/1998 | Gustilo et al. | 606/88 |
| 6,034,296 | A | * | 3/2000 | Elvin et al. | 623/16.11 |
| 6,553,681 | B2 | * | 4/2003 | Ekholm et al. | 33/551 |
| 6,610,096 | B2 | * | 8/2003 | MacDonald | 623/18.11 |
| 6,706,005 | B2 | * | 3/2004 | Roy et al. | 600/594 |
| 2003/0069644 | A1 | * | 4/2003 | Kovacevic et al. | 623/20.32 |

* cited by examiner

*Primary Examiner*—Alvin Stewart
(74) *Attorney, Agent, or Firm*—Zimmer Technology, Inc.; Jonathan Feuchtwang

(57) ABSTRACT

An implantable knee prosthesis for in-vivo measuring force components along three different axes, the X-axis, the Y-axis, and the Z-axis. The prosthesis can measure six different force components along these axes while the prosthesis is under load.

20 Claims, 3 Drawing Sheets

IMPLANTABLE PROSTHESIS FOR MEASURING SIX FORCE COMPONENTS

CROSS-REFERENCE TO RELATED APPLICATIONS

This application claims benefit of priority of U.S. Provisional Application Ser. No. 60/398,335 filed Jul. 24, 2002.

FIELD OF THE INVENTION

The disclosure herein generally relates to implantable orthopedic prostheses and, more particularly, to an implantable knee prosthesis for measuring six different force components while the prosthesis is under load.

BACKGROUND OF THE INVENTION

In the United States alone, over 200,000 knee replacements are performed each year. Degenerative arthritis, or the gradual degeneration of the knee joint, is the most common reason for these replacements. In this form or arthritis, cartilage and synovium surrounding the knee wear down so underlying bones grind directly on each other.

In knee arthroplasty, portions of the natural knee joint are replaced with prosthetic components. These components include a tibial component, a femoral component, and a patellar component. The femoral component generally includes a pair of spaced condyles that articulate with the tibial component. These condyles form a trochlear groove in which the articulating surface of the patellar component moves. The components are made of materials that exhibit a low coefficient of friction when they articulate against one another.

When the articulating ends of both the femur and tibia are replaced, the procedure is referred to as total knee replacement or TKR. Much effort has been devoted to performing TKR that restores normal, pain-free functions of the knee for the lifetime of the prosthetic components. Unfortunately, patients can experience problems with the prosthetic knee after a total knee replacement surgery. If a problem occurs, a patient may need a revision surgery wherein some or all of the prosthetic components are replaced.

Problems with a prosthetic knee can develop for a multitude of reasons. Many of these problems, though, could be eliminated or significantly diminished if scientists more thoroughly knew the dynamic forces that act on a prosthetic implant. As such, engineers and scientists devote much effort to understanding, measuring, and quantifying the forces on a prosthetic knee once it is implanted into a patient. If accurate information on these forces could be obtained, then designers could use this information to more accurately design a prosthetic knee.

Scientists have developed methods and apparatus to measure some of the forces on a prosthetic knee. U.S. Pat. No. 5,360,016 to Kovacevic and entitled "Force Transducer for a Joint Prosthesis" teaches an implantable knee prosthesis for measuring loads on the prosthesis during use. A transducer is disposed between two plates to measure axial forces on the prosthesis.

One major disadvantage with prior force measuring devices is the prosthesis can only measure forces in limited directions. The patent to Kovacevic, for example, measures axial loads on the implant. The prosthesis does not have the ability to measure three dimensional force components. In other words, forces on an implanted prosthesis actually occur along three different axes, the X-axis, the Y-axis, and the Z-axis. Measuring merely one or two of these components will not reveal a complete force distribution for the implanted prosthesis. In order to obtain this complete force distribution, forces in all three dimensions must be measured.

It therefore would be advantageous to provide implantable orthopedic prostheses that can measure three dimensional force components. Such prostheses would provide more complete measurements of the force distribution on the prosthesis.

SUMMARY OF THE INVENTION

The present invention is directed to implantable knee prostheses for in-vivo measuring force components along three different axes, the X-axis, the Y-axis, and the Z-axis. The prosthesis can measure six different load components along these axes while the prosthesis is under load. These components include the forces Fx, Fy, Fz, and the torques Tx, Ty, Tz.

The prosthesis generally comprises a tibial implant, a tibial shell, force detection instruments, and electronics. The tibial implant has a proximal end with a flat tray that has an elliptical shape. An elongated cylindrical stem extends distally from the tray. The stem is hollow and includes an opening at a distal end that leads into the hollow portion or cavity. A cap or plug is used to seal the cavity. This plug may be permanently connected to the stem, with welding for example, or removeably connected to the stem, with a press-fit or interference fit for example.

The tibial shell has a body with a cylindrical portion and a baseplate portion. A bore completely extends through the cylindrical portion from a proximal end to a distal end. The baseplate has a flat, elliptical shape that is similarly shaped to the tray portion of the tibial implant. The shell fits around the elongated stem portion of the tibial implant.

The force detection instruments are positioned inside the cavity of the cylindrical stem of the tibial implant immediately beneath or adjacent the tray. These instruments may be provided as strain gauges that are adapted to measure forces applied to the tray of the tibial implant. In the preferred embodiment, the force detection instruments are attached to an internal wall in the cavity of the stem. This portion of the stem acts as a spring element that deflects or moves when loads or forces are applied to the tray.

The electronics are positioned in the hollow portion or cavity of the stem of the tibial implant. These electronics are wired to the force detection instruments. Various electronic instruments may be provided and include, for example, an A-D converter, multiplexer, power receptor, radio transmitter, and on-board computer.

In order to assemble the components, the tibial implant and tibial shell can be connected together with an interference or tapered fit. Specifically, the stem of the tibial implant fits through the bore of the tibial shell until the tray of the implant and the baseplate of the shell are adjacent each other. Electronics and force detection instruments are then positioned inside the cavity of the stem of the tibial implant. A cap or plug then attached to the opening of the cavity to seal the electronics and instruments in the implant. The tibial implant and tibial shell can be assembled and calibrated outside of the patient. After the prosthesis is tested and validated, it can be implanted into the patient using surgical implantation techniques known in the art.

The prosthesis of the present invention measures loads on the surface of the tray portion of the tibial implant in a total knee arthroplasty (TKA) system. The force detection instruments are located on a resilient, measuring section of the cavity of the stem. This measuring section of the stem serves as a resilient, spring-like element. When loads or forces are placed on the tray, the measuring section deflects. This deflection is detected and measured with the force detection instruments. The electronics process these measurements and electronically relay the information to a computer.

One important advantage of the present invention is that a single prosthesis can measure six different load components while implanted. These load components occur along three different axes and include forces (Fx, Fy, Fz) and torques (Tx, Ty, Tz). The invention is not limited to a single axial measurement or a single torsional measurement. More comprehensive data can be measured and collected using the prosthesis of the present invention as compared to single measurement devices. This data provides a more complete account of the loads on a prosthesis while it is implanted in a patient.

DETAILED DESCRIPTION

Figure 1:
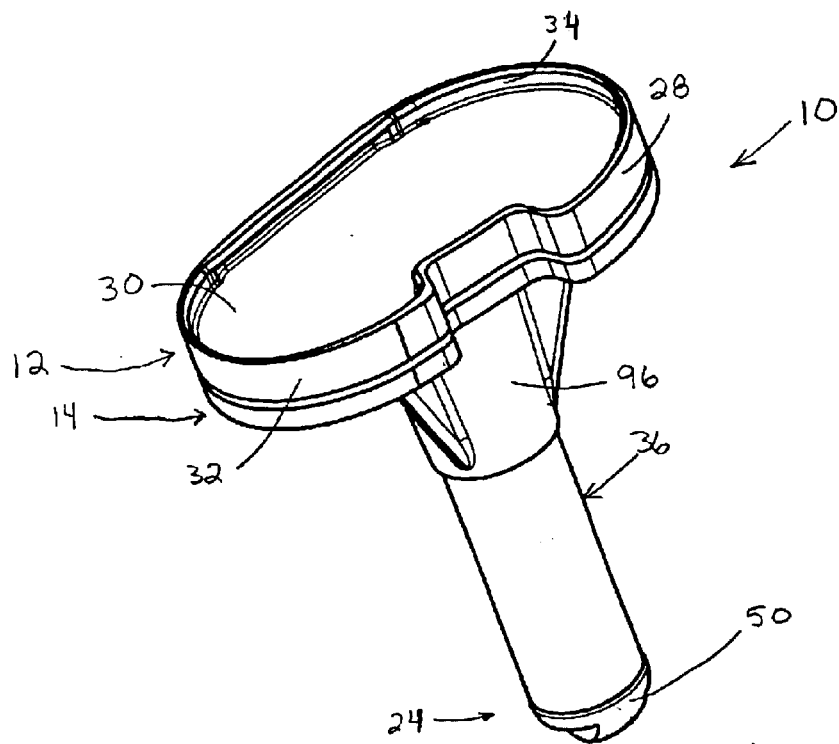
FIG. 1 is a perspective view of an implantable knee prosthesis of the present invention for measuring forces.
Figure 2:
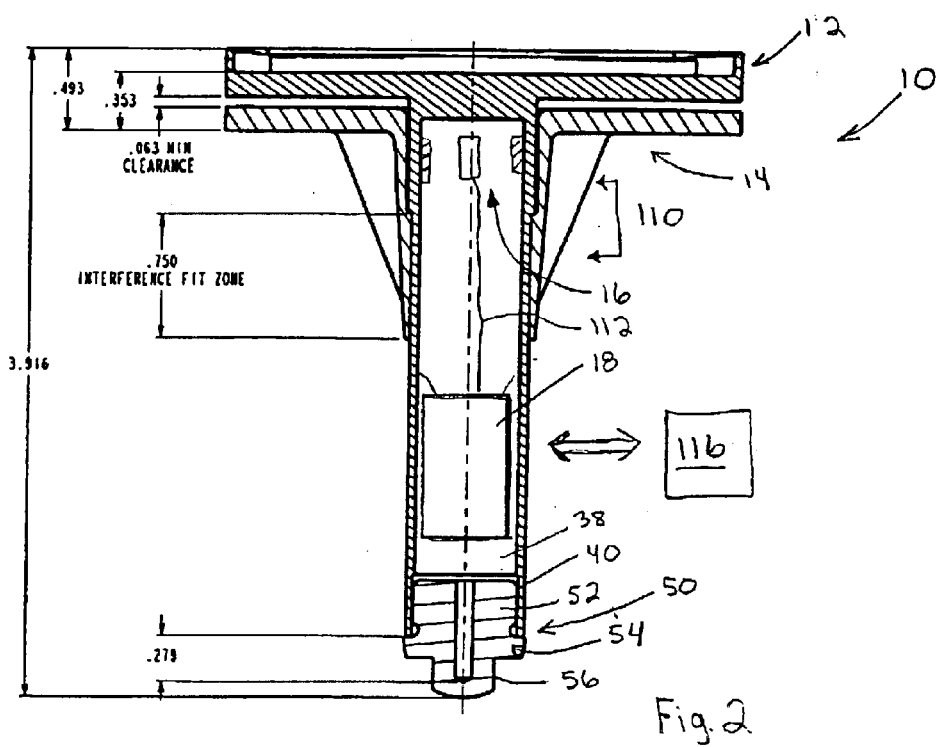
FIG. 2 is a cross sectional view of the knee prosthesis of FIG. 1 showing measurements of the prosthesis in inches.
Figure 3:
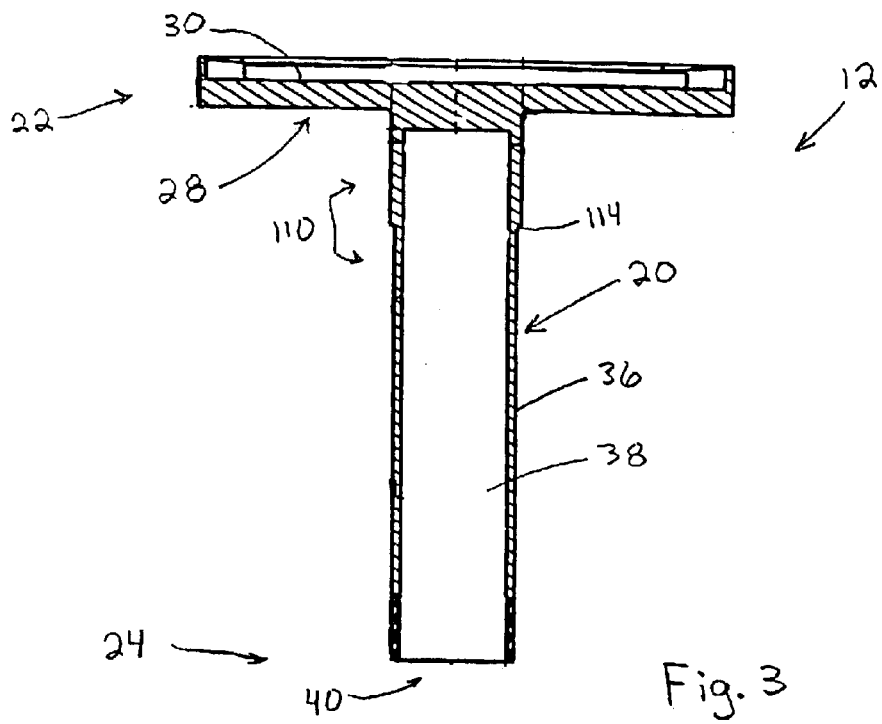
FIG. 3 is a cross sectional view of the tibial implant component of the knee prosthesis of FIG. 1.
Figure 4:
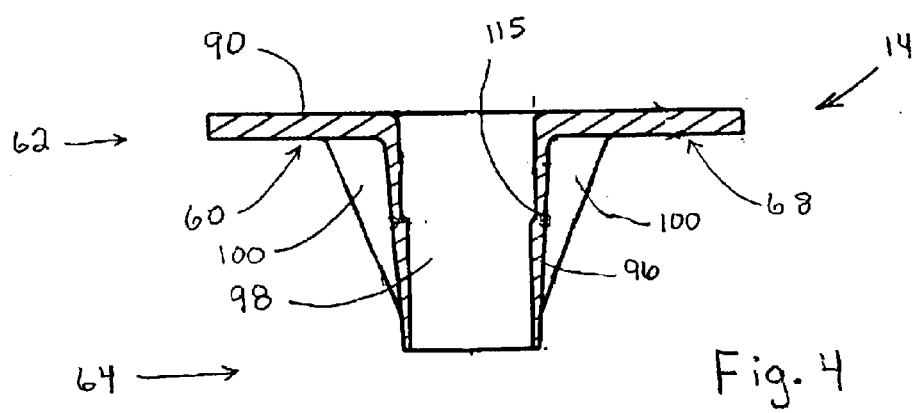
FIG. 4 is a cross sectional view of the tibial shell component of the knee prosthesis of FIG. 1.

FIGS. 1–4 show the implantable orthopedic knee prosthesis 10 of the present invention for in-vivo measuring force components. The prosthesis 10 generally includes four primary components, a tibial implant 12, a tibial shell 14, force detection instruments 16, and electronics 18.

Tibial implant 12 has a body 20 that extends from a proximal end 22 to a distal end 24. Proximal end 22 has a tray 28 with a substantially elliptical or oval shape in top view and a rectangular shape in side view. Tray 28 has a top planar surface 30. A wall 32 extends around a perimeter of the tray and forms an edge or lip 34 that extends upwardly from top surface 30. An elongated cylindrical stem 36 extends downwardly from a central portion of tray 28. Stem 36 has a smooth outer surface with an internal cavity 38. The cavity has an elongated cylindrical shape and extends from the distal end 24 upwardly toward the proximal end 22. An opening 40 is located at the distal end 24 and provides access to the cavity 38.

A cap or plug 50 is provided to seal the distal end 24 of tibial implant 12 and cavity 30. The plug has a cylindrical portion 52 that is adapted to fit into opening 40. A shoulder 54 on the plug abuts against the end wall of the distal end. A knob portion 56 is provided to grip the plug in order to insert and remove it from opening 40. The plug is designed to removeably press-fit into opening 40 and seal cavity 38.

One skilled in the art will appreciate that the connection between the plug 50 and tibial implant 12 can have a variety of configurations. For example, the cylindrical portion 52 of the plug can have external threads to threadably mate with internal threads located in cavity 38 at the distal end 24. Alternatively, the plug can be designed to be permanently affixed to the tibial implant. The plug, for example, can be welded to the implant.

Tibial shell 14 has a body 60 that extends from a proximal end 62 to a distal end 64. Proximal end 62 has a baseplate 68 with a substantially elliptical or oval shape in top view and a rectangular shape in side view. Baseplate 68 is similarly configured to the tray 28 and has a top planar surface 90. A cylindrical stem 96 extends downwardly from a central portion of baseplate 68. Stem 96 has a smooth outer surface with an internal bore 98 that extends completely through the body from the proximal end 62 to the distal end 64. The bore has a cylindrical shape that is adapted to receive stem 36 of tibial implant 12. Two fins or shoulders 100 extend from an external surface of stem 96 to the underside of baseplate 68. The fins provide rotational and translational stability while the prosthesis is implanted in the bone. One skilled in the art will appreciate that these fins can have various shapes and sizes. For example, the fins can be replaced with pockets or pegs. Further, rotational and translational stability can be provided at numerous locations on the exterior of the prosthesis.

One skilled in the art will appreciate that the tibial implant and shell can have various configurations known in the art. These configurations can be adapted to measure the six load components of the present invention. Tibial implant 12 and tibial shell 14 of the figures illustrate one embodiment.

The force detection instruments 16 and electronics 18 are positioned inside cavity 38 of tibial implant 12. The force detection instruments are located adjacent the tray 28 along a measuring section 110. These instruments may be provided as strain gauges, such as resistant strain gauges. One skilled in the art will appreciate that the force detection instruments can be any type of instrumentation used to detect forces or loads. Other than strain gauges, other force detection instruments such as semiconductor based forces sensors or piezoelectric sensors can also be used.

Force detection instruments 16 are connected via wires 112 to the electronics 18. The electronics can include various devices known to be used with the force detection instrumentation. Preferably, the electronics include an A-D converter, multiplexer, power receptor, radio transmitter, filters, temperature compensation, and on-board computer.

The tibial implant and tibial shell can be connected together with an interference fit, tapered fit, welded, threaded, adhesive, or other fixation method known in the art. Specifically, stem 36 of the tibial implant includes a section 114 that is adapted to engage a corresponding section 115 in the internal surface of cylindrical portion 96. As shown best in FIG. 2, the tibial implant and shell form a fixation zone or interference fit zone. One skilled in the art will appreciate that these components can be removeably or permanently connected together in a variety of ways without departing from the scope of the invention.

Electronics 18 and force detection instruments 16 are positioned and affixed inside the cavity 38 of the stem 36 of the tibial implant 12. The electronics and instruments can be, for example, glued to the internal wall of cavity 38. The plug 50 is then attached to the opening 40 of the cavity to seal the electronics and instruments in the tibial implant. The tibial shell and distal stem may then be cement retained to the tibia.

One advantage of the present invention is that the force measuring section 110 is integrally part of the implantable prosthesis itself. In other words, no separate component is required. More particularly, measuring section 110 is formed as part of the stem 36 of tibial implant 12. In use, measuring section 110 acts or functions as a resilient, spring-like element. When loads or forces are placed on the tray 28, the measuring section deflects. This deflection is detected and measured with the force detection instruments. The electronics process these measurements and electronically relay the information or data to a computer 116. The computer stores the data for documentation and analysis purposes.

Figure 5:
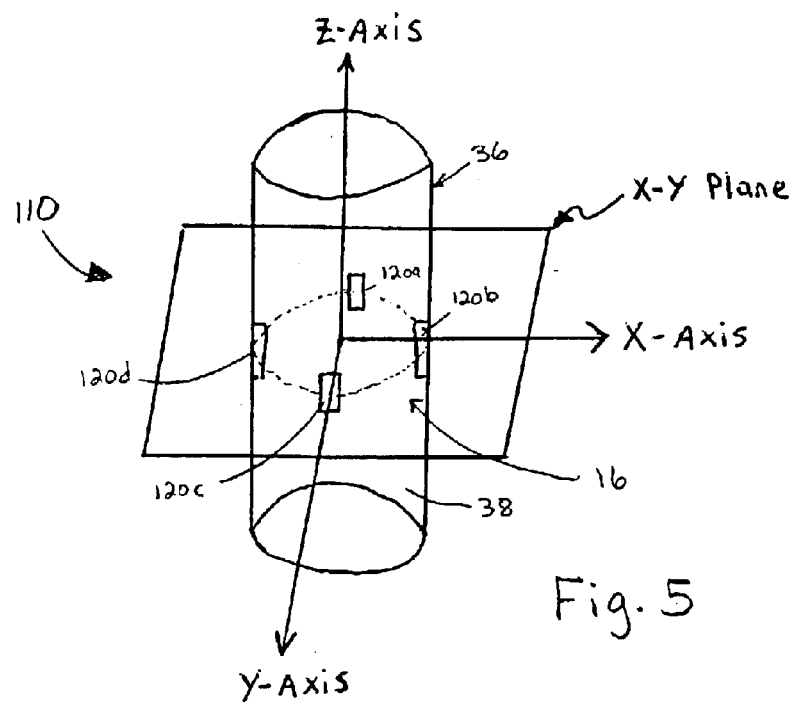
FIG. 5 is an enlarged view of the measuring section of the tibial implant component showing the placement of force detection instruments.

FIG. 5 shows an enlarged view of the measuring section 110 of stem 36. Force detection instruments 16 are shown as four strain gauges 120a–120d. These gauges are equally and circumferentially spaced along the inner wall of stem 36 in cavity 38. The gauges are placed in the X-Y plane as shown.

Selecting the best position and configuration for the gauges will necessitate a tradeoff between having more gauges to increase the accuracy of the measurements and fewer gauges to accommodate limitations of data acquisition. While three gauges are needed to completely define the strain state on the surface of the measuring section, the free body diagram analysis of the loads indicate that the tangential strain component is not directly loaded by any of the applied loads. Thus, only measurements that define the axial and shear strains are necessary. These two components can then be measured using any combination of gauges sensitive to axial and shear strain. Combinations of gauges that are either aligned with the Z-axis or 45 degrees from the Z-axis satisfy this requirement while making the measurements easier to interpret without computational aid. For example, a gauge on the Z-axis provides the axial strain directly.

Figure 6:
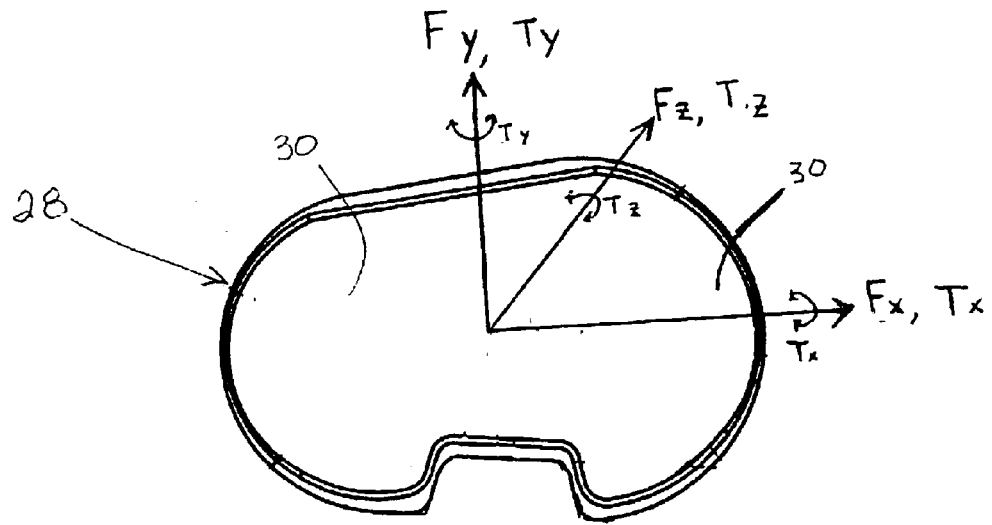
FIG. 6 is a top view of the tibial implant component with a force diagram showing six different force components.

One important advantage of the present invention is that the prosthesis 10 can measure six different force components. Looking also to FIG. 6, three different axes are shown as X-axis, Y-axis, and Z-axis. Each axis has two force components, a force designated as F and a torque designated as T. Thus, the six force components are divided as Fx and Tx (force and torque along the X-axis), Fy and Ty (force and torque along the Y-axis), Fz and Tz (force and torque along the Z-axis). These force components are shown as they appear on the tray 28 of the tibial implant.

To completely define the applied six force components a minimum of six independent equations are necessary. These equations may be developed by considering three gauge locations located 120 degrees apart along the measuring section 110. The gauges need to provide a measure for the axial (Z-axis) and shear strain component. The resulting six strains will be independent and sufficient for defining the stiffness matrix needed to predict the loading. This configuration also requires the least data acquisition requirements, and will allow for faster data collection rates when multiplexing.

While the minimum configuration of three gauges located 120 degrees apart makes load prediction possible, the preferred configuration uses four gauges. As shown in FIG. 5, these gauges are located on a transverse plane and at the intersections of the X-Z and Y-Z planes. The advantage to the configuration shown in FIG. 5 is that the strain values are directly related to the applied load components. For example, locations on the X-Z plane give the direct strain value caused by an X-axis force, and these locations are completely independent of any Y-axis force component.

Complete determination of the true strains is possible if an axial, +45°, and −45° strain gauge configuration is used in the orientation shown in FIG. 5. This configuration has 12 total gauges so the data acquisition considerations will be at least two times larger. However, the redundancy of the configurations also allows weighting of gauges that have better response characteristics.

For reporting and analysis purposes, the gauge readings are described as Axial (along the Z-axis), Tangential (hoop stress in the X-Y plane), or Shear (in the X-Z or Y-Z plane depending on the gauge location). Axial and Tangential positive strains indicate tension. Shear strains that result from positive torques or bending moments are positive. The coordinate system of the tray 28 is located on the transverse plane that is defined on the top surface 30. The origin of the coordinate system is in this plane, at the intersection of the line dividing the anterior-posterior portions of the tray and the line dividing the medial-lateral portions of the tray. The positive Y-axis then coincides with the medial-lateral dividing line in the anterior direction, and the positive X-axis coincides with the anterior-posterior dividing line in the lateral direction. The positive Z-axis then extends inferiorly from the origin of the coordinate system. With this coordinate system, the analytical determination for the stress due to each load component is described in Table 1 below. Strain is then predicted from stress by simply applying the linear modulus of the material to each stress component.

TABLE 1

Analytical solutions for the stresses acting on the measuring section

| | |
|---|---|
| Z Axis Force<br>Axial stress = Fz/A<br>Bending stress: none<br>Tangential stress = vFz/A<br>Shear stress: none | 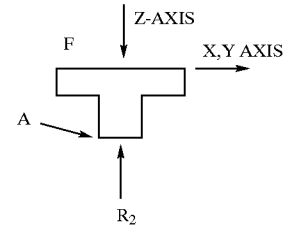<br>$\Sigma F_z = 0$:   R - F<br>$\sigma = F/A$   $\tau = 0$ |
| Z Axis Torque<br>Axial stress: none<br>Bending stress: none<br>Tangential stress: none<br>Shear stress: = TzP/J | 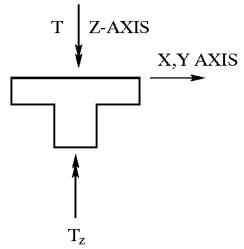<br>$\Sigma T_z = 0$   $T_z = T$<br>$\tau = T_p/J$   $\sigma = 0$ |
| X and Y Axis Forces<br>Axial stress: none<br>Bending stress = (Fr)c/I<br>Tangential stress = v(Fr)c/I<br>Shear stress: F/A | 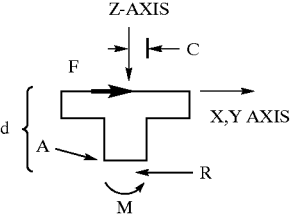<br>$\Sigma F_{x,y} = 0$   $R_{x,y} = F$<br>$\Sigma T_{x,y} = 0$   $T_{x,y} = F \times d$<br>$\sigma_{+c,-c} = \pm(Fd)C/I$   $\tau = F/A$ |

TABLE 1-continued

Analytical solutions for the stresses acting on the measuring section

X and Y Axis Torques
Axial stress: none
Bending stress = Tc/I
Tangential stress = vTc/I
Shear stress: none $\Sigma T_{x,y} = 0 \quad T_{x,y} = T$ $\sigma_{+c,-c} = \pm Tc/I \quad \tau = 0$ Using the principle of superposition for a linear system, complex loading from multiple load components can be simplified by considering each load component separately to determine the resulting stress and strain. Then, the strains from each component can be summed to determine the actual combined loading state.

Superimposing each load component yields the matrix that will completely define the three dimensional strain on the stem for any combination of loads applied to the tray. This matrix is denoted as the stiffness matrix and is presented in analytical form in Table 2 for the preferred cross section.

TABLE 2

The Stiffness Matrix for the preferred orientation

| % Fx | % Fy | % Fz | % Tx | % Ty | % Tz | Strain Location | Strain Type |
|---|---|---|---|---|---|---|---|
| 0 | 0 | 0 | 0 | 0 | 0 | Anterior | Tang |
| c/(G*As) | 0 | 0 | 0 | 0 | p/(G*J) | Anterior | Shear |
| 0 | r*c/(E*I) | 1/(E*Ac) | c/(E*I) | 0 | 0 | Anterior | Axial |
| 0 | 0 | 0 | 0 | 0 | 0 | Medial | Tang |
| 0 | c/(G*As) | 0 | 0 | 0 | p/(G*J) | Medial | Shear |
| r*c/(E*I) | 0 | 1/(E*Ac) | 0 | c/(E*I) | 0 | Medial | Axial |
| 0 | 0 | 0 | 0 | 0 | 0 | Posterior | Tang |
| c/(G*As) | 0 | 0 | 0 | 0 | p/(G*J) | Posterior | Shear |
| 0 | r*c/(E*I) | 1/(E*Ac) | c/(E*I) | 0 | 0 | Posterior | Axial |
| 0 | 0 | 0 | 0 | 0 | 0 | Lateral | Tang |
| 0 | c/(G*As) | 0 | 0 | 0 | p/(G*J) | Lateral | Shear |
| r*c/(E*I) | 0 | 1/(E*Ac) | 0 | c/(E*I) | 0 | Lateral | Axial |

C, P is the distance of the stress element from the neutral axis.
Ac, As are cross sectional area of the spring.
R is the distance from the applied load to the stress element.
G, E are the moduli of the spring material.
I, J are the inertias for the respective stress calculation.

Once the strain matrix has been determined, the loads that produce a measured strain can be calculated. First, the measured strains must be converted into the strain coordinate system used to determine the stiffness matrix.

For a three gauge rosette, the transformation equations are:

$EA = Etan*\cos 2A + Eaxl*\sin 2A + Eshr*\sin t*\cos A$ $EB = Etan*\cos 2B + Eaxl*\sin 2B + Eshr*\sin t*\cos B$ $EC = Etan*\cos 2C + Eaxl*\sin 2C + Eshr*\sin t*\cos C$ In these equations, A, B, and C are angles describing the orientation of the gauges A, B, and C, that each measure strains EA, EB, and EC. Etan, Eaxl, and Eshr are the tangential strains, axial strains, and shear strains described in the stiffness matrix (referred to as the engineering strains). This transformation is necessary because the rosette gauges do not directly measure shear strains. The strains are then multiplied by the stiffness matrix to predict force. This will completely describe the three dimensional loading on the measuring section 110 that results from loads applied to the top surface 30 of tray 28.

A statistical method is also possible to define the stiffness matrix. If a combination of at least six independent strain measurements can be achieved, then the stiffness matrix relating those strains to the input load can be determined by performing the least squares regression between the load matrix and the strain matrix. With perfect gauge placement and bonding, the resulting analytical, FE, and statistical strain matrixes will be identical for identical measuring sections and gauge placements.

The present invention is described using an implantable orthopedic knee prosthesis. As another advantage, the principles of the present invention can be applied to other implantable devices as well. For example, the principles of the present invention can be applied to other designs for knee prostheses, aside from the knee prosthesis shown and described in connection with FIGS. 1–6. Further, other prostheses can also be used, such as implantable femoral hip prostheses, ankle prostheses, or shoulder prostheses.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. An implantable knee prosthesis for measuring force components, comprising:
   a tibial implant having a tray and an elongated stem extending distally from the tray, the stem has an internal cavity and a force measuring section; and
   at least one force detection instrument located in the internal cavity at the force measuring section, wherein the force detection instrument is adapted to measure six different force components while the tibial implant is under load.

2. The knee prosthesis of claim 1 wherein the force measuring section is integrally formed with the stem.

3. The knee prosthesis of claim 2 wherein the force detection instrument measures deflection of the force measuring section.

4. The knee prosthesis of claim 1 wherein the force detection instrument includes four measuring sensors equally spaced and circumferentially disposed in the cavity.

5. The knee prosthesis of claim 4 wherein the measuring sensors are strain gauges.

6. The knee prosthesis of claim 1 wherein a coordinate system having an X-axis, Y-axis, and Z-axis define the tray, and the force detection instrument is adapted to measure force components along the X, Y, and Z axes.

7. The knee prosthesis of claim 6 wherein the force components includes forces and torques along the X, Y, and Z axes.

8. The knee prosthesis of claim 1 wherein the force measuring section is adjacent the tray.

9. An implantable prosthesis for measuring loads while implanted, the prosthesis comprising:
- a first component adapted to be affixed to bone; and
- a second component connectable to the first component, the second component including an elongated stem having a force measuring section and an internal cavity, at least one force detection instrument located in the cavity, and electronics located in the cavity and connected to the force detection instrument, wherein the force detection instrument measures six different force components defined along a coordinate system having an X-axis, Y-axis, and Z-axis.

10. The implantable prosthesis of claim 9 wherein force components include forces and torques along all of the X, Y, and Z axes.

11. The implantable prosthesis of claim 9 wherein the force measuring section is integrally formed with the stem.

12. The implantable prosthesis of claim 11 wherein the force detection instrument measures strain along the force measuring section.

13. The implantable prosthesis of claim 12 wherein the force measuring section is formed as a hollow cylinder.

14. The implantable prosthesis of claim 9 wherein the second component includes an enlarged substantially elliptical tray, and the force measuring section is adjacent the tray.

15. An implantable knee prosthesis for measuring force components, comprising:
- a tibial implant having an enlarged tray and an elongated stem extending downwardly from the tray, the stem having an internal cavity and a force measuring section;
- a tibial shell adapted to be implanted into an intramedullary canal of a tibia, the tibial shell connected to the tibial implant; and
- at least one force detection instrument located in the internal cavity at the force measuring section, wherein the force detection instrument is adapted to measure multiple force components while the tibial shell is implanted and the tibial implant is under load.

16. The implantable knee prosthesis of claim 15 wherein the force detection instrument measures six different force components in a coordinate system with X, Y, and Z axes.

17. The implantable knee prosthesis of claim 16 wherein two different force components are measured in each of the X, Y, and Z axes.

18. The implantable knee prosthesis of claim 15 wherein the tibial shell has a cylindrical portion with a bore adapted to receive and engage the stem of the tibial implant.

19. The implantable knee prosthesis of claim 18 wherein tibial shell has a baseplate similarly shaped to the tray of the tibial implant.

20. The implantable knee prosthesis of claim 15 wherein the tibial implant is removeably connectable to the tibial shell while the tibial shell is implanted.

* * * * *